United States Patent
Childre et al.

(10) Patent No.: US 8,123,696 B2
(45) Date of Patent: Feb. 28, 2012

(54) PHYSIOLOGICAL COHERENCE IN ANIMALS

(75) Inventors: Doc L. Childre, Boulder Creek, CA (US); Rollin McCraty, Boulder Creek, CA (US); Michael A. Atkinson, Boulder Creek, CA (US); David Joffe, Boulder, CO (US)

(73) Assignee: Quantum Intech, Inc., Boulder Creek, CA (US)

( * ) Notice: Subject to any disclaimer, the term of this patent is extended or adjusted under 35 U.S.C. 154(b) by 1251 days.

(21) Appl. No.: 11/881,171

(22) Filed: Jul. 25, 2007

(65) Prior Publication Data

US 2007/0270668 A1 Nov. 22, 2007

Related U.S. Application Data (63) Continuation-in-part of application No. 11/528,955, filed on Sep. 27, 2006, now Pat. No. 7,462,151, which is a continuation of application No. 10/486,775, filed as application No. PCT/US00/05224 on Mar. 1, 2000, now Pat. No. 7,163,512, which is a continuation of application No. 09/260,643, filed on Mar. 2, 1999, now Pat. No. 6,358,201.

(60) Provisional application No. 60/833,393, filed on Jul. 25, 2006.

(51) Int. Cl.
*A61B 5/02* (2006.01)
*A61B 5/00* (2006.01)

(52) U.S. Cl. ......... 600/500; 600/300; 600/481; 600/508
(58) Field of Classification Search .................. 600/300, 600/301, 481, 508, 529; 119/856–865
See application file for complete search history.

(56) References Cited

U.S. PATENT DOCUMENTS 5,370,082 A * 12/1994 Wade ............................ 119/859

OTHER PUBLICATIONS

Tiller et al. "Cardiac Coherenece: A New, Noninvasive Measure of Autonomic Nervous System Order", Alternative Therapies. Jan. 1996. vol. 2, No. 1. pp. 52-65.*
Allen et al. "Cardiovascular Reactivity and the Presence of Pets, Friends, and Spouses: The Truth About Cats and Dogs", Psychosomatic Medicine. 2002. 64:727-739.*

* cited by examiner

*Primary Examiner* — Miranda Le
*Assistant Examiner* — Tiffany Weston
(74) *Attorney, Agent, or Firm* — Dickstein Shapiro LLP

(57) ABSTRACT

A coherence value or category for an animal subject is calculated, and a corresponding coherence indication is provided to a human subject. In one embodiment, the beat-to-beat changes in the animal subject's heart rate is monitored, and used to calculate a coherence value, which may be representative of a coherence category. The coherence value may be determined by the power distribution of the heart rate variability data for the animal subject. In another embodiment, the degree of synchronization between an animal subject's coherence and an associated human subject's coherence may be determined and provided as feedback.

22 Claims, 10 Drawing Sheets

PHYSIOLOGICAL COHERENCE IN ANIMALS

CROSS REFERENCE TO RELATED APPLICATION

This application is a continuation-in-part of U.S. patent application Ser. No. 11/528,955, filed on Sep. 27, 2006, which is a continuation of U.S. patent application Ser. No. 10/486,775, filed Feb. 13, 2004, now U.S. Pat. No. 7,163,512, which is the National Stage of International Application No. PCT/US00/05224, filed Mar. 1, 2000, which is a continuation of U.S. application Ser. No. 09/260,643, filed Mar. 2, 1999, now U.S. Pat. No. 6,358,201. This application also claims the benefit of U.S. Provisional Patent Application No. 60/833,393, filed on Jul. 25, 2006.

FIELD OF THE INVENTION

The invention relates to detecting and measuring changes in the level of physiological coherence (also referred to as nervous system synchronization, entrainment or resonance) and/or emotional states in animals.

BACKGROUND OF THE INVENTION

In U.S. Pat. No. 6,358,201, entitled "Method and Apparatus for Facilitating Physiological Coherence and Autonomic Balance," which is assigned to the assignee hereof and hereby incorporated fully by reference, it was shown that the body's systems such as blood pressure rhythms (measured by recording pulse transit time (PTT), the heart (measured by a heart rate variability (HRV)), and the respiration system (measured by the respiration rate) can all entrain or synchronize, which is representative of a state of physiological coherency. Furthermore, in humans they all synchronize to a frequency varying around 0.1 Hertz (Hz) when the subject is experiencing a positive emotional state or is deeply relaxed. Thus, one can intentionally bring these systems, acting as coupled biological oscillators, into synchronization with each other. In addition, in this coherent or resonant mode, several brain rhythms (measured by an electroencephalograph (EEG)) become more synchronized to the heart.

This is significant because there are a number of health benefits conferred by physiological coherence or resonance. For example, there is increased cardiac output in conjunction with increased efficiency in fluid exchange, filtration, and absorption between the capillaries and tissues; increased ability of the cardiovascular system to adapt to circulatory requirements; and increased temporal synchronization of cells throughout the body. This results in increased system-wide energy efficiency and metabolic energy savings. These findings provide a link between positive emotions and increased physiological efficiency, which may partly explain the growing number of correlations documented between positive emotions, improved health, and increased longevity.

However, heretofore there has been little recognition that animals also experience emotional states and, as such, their feelings and emotions affect physiological processed and rhythms and which affect their level or degree of physiological coherency. In addition, there is little appreciation of the emotional link experienced between animals and humans, such as between a pet and their owner. Accordingly, there is a need for the detection, measurement and facilitation of emotional wellbeing and/or physiological coherency in animals.

BRIEF SUMMARY OF THE INVENTION

Systems and methods for detecting and measuring physiological coherence in animals is disclose d and claimed herein. In one embodiment, a method includes sampling a physiological measure of an animal subject, deriving a power spectrum distribution (PSD) from the physiological measure, and tracking dynamically a PSD peak within a predetermined range where the PSD peak has a relative amplitude to a plurality of other peaks in the PSD. The method further includes determining a current coherence value based on the relative amplitude and corresponding to the animal subject's parasympathetic activity, and determining a current coherence category for the animal subject from a plurality of coherence categories which corresponds to the current coherence value. Thereafter, a coherence category indication associated with the current coherence category is provided by the method.

In another embodiment, a method for detecting a physiological coherence shift in an animal subject includes sampling, at a first time, a physiological measure of the animal subject, and generating a heart rate variability (HRV) waveform based on the sampling at the first time, wherein the HRV waveform has a first pattern. The method further includes sampling, at a second time, the physiological measure of the animal subject, and updating the HRV waveform based on the sampling at the second time, wherein the HRV waveform has a second pattern. In addition, the method includes comparing the first pattern to the second pattern to detect a coherence change in the animal subject, and providing a coherence indication associated with the coherence change.

Other aspects, features, and techniques of the invention will be apparent to one skilled in the relevant art in view of the following detailed description of the invention.

DETAILED DESCRIPTION OF EXEMPLARY EMBODIMENT

As disclosed in the previously-incorporated U.S. Pat. No. 6,358,201, Freeze-Frame® is one tool that may be used for mental and emotional self-management and performance enhancement. It consists of consciously disengaging the mental and emotional reactions to either external or internal events and then shifting one's center of attention to the physical area around the heart and breathing as if you are breathing out through the solar plexus. These steps facilitate a shift in the heart's rhythmic beating pattern. The next step is to intentionally shift one's emotional state by focusing on a positive emotion such as love, care or appreciation. In one embodiment, this positive emotional shift stabilizes the coherent physiological mode and takes the process past what can be achieved with breathing techniques alone. This tool thus allows the individual to shift focus of attention from the mind to the heart. Such a shift results in a wider and more objective perception in the moment.

One aspect of the present disclosure is to extend these concepts to the detection and measurement of emotional state and/or stress/relaxation levels in animals, including pets. In certain embodiments, this emotional state may be measured using some physiological indicator(s) (e.g., animal skin conductance, heart rate, heart rate variability, HRV coherence and/or respiratory rate/pattern information), where the resulting data may be interpreted in light of known values that correlate to specific emotional states and/or stress levels. By way of example, various types of pattern data based on the physiological indicator measurements may be interpreted in light of known patterns. It should further be appreciated that such analysis may be carried out in the frequency domain, the time domain, using a non-linear approach, using period analysis, using template matching, etc.

In certain other embodiments, it may be desirable to facilitate physiological coherence (as described below) and/or emotional wellbeing in animals using any known feedback mechanism. While in the principles set forth herein should be understood to apply to all animals, they may be particularly applicable to dogs, cats, horses and other pet-type animals.

Additionally, coherence may be reflected in the patterns of physiological activity. To that end, another aspect of the invention is to detect changes in patterns of physiological activity rather than changes in activation levels of physiological activity such as increased or decreased skin conductance or changes in heart rate. The patterns of activity can be detected in respiratory activity, blood pressure rhythms or patterns that emerge in the beat to beat changes in heart rate which is referred to as heart rate variability, or analysis of heart rate accelerations and deaccelerations over a shorter time scale. Coherence (which includes and embraces the concepts resonance, entrainment and synchronization) reflects increased order or harmony occurring within and among various physiological systems.

Another aspect of the present disclosure is the simultaneous measurement of human (e.g., pet owner) and animal physiological indicators to detect and/or measure the level of synchronization, physiological linkage, coherence or other indicators of physiological or emotional linkage between the animal and the human. Indeed, the emotional link between animals and humans may at least in part explain why pet owners have repeatedly been shown to have better health than non-pet owners.

Still another aspect of the invention is the notion of detecting and indicating meta-coherence when present. That is, if one signal changes in some way generally coincident with changes in the second signal, but the two signals in question are quite different from each other in the time and thus frequency domains, then "coincident changing" could be defined as a kind of meta-coherence, rather than the close tracking of one signal by the other in the time or frequency domain.

As used herein, term "coherence" refers to a more ordered mental and emotional process as well as more ordered and harmonious interactions among various physiological systems. In this context, "coherence" embraces many other terms that are used to describe specific functional modes, such as synchronization, entrainment, and resonance.

Many contemporary scientists believe that the quality of feeling and emotion we experience in each moment is rooted in the underlying state of our physiological processes. This of course was the essence of the theory of emotion first proposed by William James more than a century ago. Recent expression of this view is expounded by neuroscientist Antonio Damasio (2003: 131): "The fact that we, sentient and sophisticated creatures, call certain feelings positive and other feelings negative is directly related to the fluidity or strain of the life process." The feelings we experience as "negative" are indicative of body states in which "life processes struggle for balance and can even be chaotically out of control." By contrast, the feelings we experience as "positive" actually reflect body states in which "the regulation of life processes becomes efficient, or even optimal, free-flowing and easy."

Thus, a human or animal's experience of stress and anxiety, feelings of calm and relaxation or experience of more optimal states, commonly referred to as "the zone" or "flow," are fundamentally rooted in the emotional processing of the body's response to both external and internal stimuli. In these terms, the experience fear, pain, stress, anxiety, etc. is a struggle to maintain physiological harmony (homeostasis) and self-control in the face of a threatening challenge. In turn, these "negative" emotional feelings are reinforced by the body's experience of the physiological responses activated during this state: decreased coherence in heart and respiratory rhythms, increased heart rate, rise in adrenaline and other stress hormones, and so forth. Through this reciprocal interaction, this "strained" psychophysiological state, experienced as a negative feeling.

If, on the other hand, the animal is able to activate a positive emotion and thereby shift their bodily state to one of increased "fluidity"—synchronization and harmony in the activity of the body's somatosensory systems and subsystems—this changed psychophysiological milieu serves to generate, reinforce, and stabilize a "positive" feeling state. The result of this shift is an optimal psychophysiological state reflected as increased coherence.

Research has demonstrated that the output control signals of the sympathetic system, which is responsible for increased heart rate and blood pressure, such as in response to perceived danger, tend to be relatively low frequency rhythms. In contrast, the parasympathetic system, which operates to limit or suppress the effects of the sympathetic system, tend to be relatively high frequency signals. In general, the parasympathetic system tends to produce a relaxed state whereas the sympathetic a more active, excited state. For example, on inhalation, the parasympathetic system is inhibited and the sympathetic system is more active, resulting in an increase in heart rate. In contrast, on exhalation, the parasympathetic system is active, resulting in a stronger parasympathetic signal to the heart and heart rate is decreased.

The brainstem also receives afferent information from the baroreceptor network, and other receptor neurons, located throughout the heart and in the aortic arch of the heart, which are sensitive to stretch (pressure) and chemical changes within the heart. As the heart beats, and its walls swell, various baroreceptors are triggered, providing signals as a function of the heart beat, where increased heart rate is generally reflected by increased baroreceptor signals.

In response to the parasympathetic and sympathetic control signals from the brainstem, the heart rate varies. The sinus node (SN) of the heart is a group of cells which act as a natural pacemaker to initiate the onset of the heart beat at a rate which is non-linearly related to the relative strengths of these autonomic control signals. It has been determined that the heart beats with a certain variability, where the time between beats is not constant but rather varies according to the shifting relative balance between the parasympathetic and sympathetic signals.

Physiological coherence is characterized by both autocoherence and cross-coherence in the activity of physiological systems. For example, this mode is associated with increased coherence in breathing rhythms and the heart's rhythmic activity, which in an optimal state manifests as a sine wave-like heart rhythm pattern (autocoherence) which can be detected and recognized via various signal processing methods. Additionally, during this mode there also tends to be increased cross-coherence or entrainment among different physiological oscillatory systems, including the heart rhythms, respiratory rhythms, and blood pressure waves.

A related phenomenon that occurs during physiological coherence is resonance. In physics, resonance refers to a phenomenon whereby an unusually large vibration is produced in a system in response to a stimulus whose frequency is the same as, or nearly the same as, the natural vibratory frequency of the system. When analyzed in the frequency domain, the frequency of the vibration produced in such a state is said to be the resonant frequency of the system. When the animal system is operating in the coherent mode, increased synchronization occurs between the sympathetic and parasympathetic branches of the autonomic nervous system (ANS), and entrainment occurs among the heart rhythms, respiratory rhythms, and blood pressure oscillations and can also occur among very low-frequency brain rhythms, and electrical potentials measured almost anywhere across the skin. This occurs because these oscillatory subsystems are all vibrating at the resonant frequency of the system. However, there is a range (the "coherence range") in which the coherent mode can be observed in the majority of subjects, animal and human alike. It is likely that this specific range will vary by animal-type. When a subject is functioning in the coherent mode, there is a variability in the non-linear rhythms (respiratory, blood pressure or heart rhythm), which for humans and at least some animals will be in the coherence range of 0.03125 Hertz and 0.234 Hertz. However, it should be appreciated that the coherence range may vary depending on the type of animal. In addition, the coherence range may be similarly represented in the time domain.

In terms of physiological functioning, physiological coherence or resonance confers a number of benefits to the system. For example, there is increased cardiac output in conjunction with increased efficiency in fluid exchange, filtration, and absorption between the capillaries and tissues; increased ability of the cardiovascular system to adapt to circulatory requirements; and increased temporal synchronization of cells throughout the body. This results in increased system-wide energy efficiency and metabolic energy savings. Thus, there exists a link between positive emotions and increased physiological efficiency, which may partly explain the growing number of correlations documented between positive emotions, improved health, and increased longevity.

Physiological coherence may be characterized by a narrow band high amplitude signal in the low frequency (LF) region of the HRV power spectrum, with no other significant peaks in the very low frequency (VLF) or high frequency (HF) region, and a relatively harmonic signal (sine-wave-like), in the time domain trace of the HRV data. However, other forms of pattern data may equally be used in the detection and measurement of emotional state and/or stress levels in animals.

As discussed above, one aspect of the present disclosure is to extend these concepts to the detection and measurement of emotional state and/or stress levels in animals, and to the facilitation of physiological coherence and/or emotional wellbeing in animals. To that end, in one embodiment, a physiological indicator (e.g., animal's skin conductance, heart rate, heart rate variability, HRV coherence and/or respiratory rate/pattern information) is measured and used as an indication of the animal's emotional state and/or emotional well-being. ECG, pulse and/or respiration sensors (e.g., chest strap, fabric strap with ECG sensors, optical sensors, implantable sensors, etc.) can be embedded in or attached to a harness that extends around the chest-belly of the animal. Alternatively, heart rate or respiration sensors can be incorporated into collars or other wearable devices. The processing of the signals and displays for feedback in this case may be contained locally on the animal (e.g. display is on the collar or harness). The feedback display can be a light emitting diode (LED) strip showing rate and rhythm, sound, multi-colored LED's, etc.

Alternatively, the physiological sensors can transmit the data to a portable display such as a device built specifically for this purpose, a watch, cell phone, PC or any other such device for processing and displaying the data, via any known wireless communication protocol.

As also mentioned above, another aspect of the present disclosure is to perform the simultaneous measurement of human (e.g., pet owner) and animal (e.g., pet) physiological indicators to detect and/or measure the level of synchronization, coherence or other indicators of physiological or emotional linkage between the animal and the human. In one embodiment, this may be performed by simultaneously detecting the physiological indicators from a human and an animal. Feedback on the degree of linkage can be displayed with LED's, sound, light sources, computer feedback displays, graphic displays (e.g. indicators from the pet and owner showing degree of synchronization, and or coherence, and/or displays that show the indicators either diverging or converging.

As used herein, the terms "a" or "an" shall mean one or more than one. The term "plurality" shall mean two or more than two. The term "another" is defined as a second or more. The terms "including" and/or "having" are open ended (e.g., comprising). Reference throughout this document to "one embodiment", "certain embodiments", "an embodiment" or similar term means that a particular feature, structure, or characteristic described in connection with the embodiment is included in at least one embodiment of the present invention. Thus, the appearances of such phrases in various places throughout this specification are not necessarily all referring to the same embodiment. Furthermore, the particular features, structures, or characteristics may be combined in any suitable manner on one or more embodiments without limitation. The term "or" as used herein is to be interpreted as inclusive or meaning any one or any combination. Therefore, "A, B or C" means "any of the following: A; B; C; A and B; A and C; B and C; A, B and C". An exception to this definition will occur only when a combination of elements, functions, steps or acts are in some way inherently mutually exclusive.

In accordance with the practices of persons skilled in the art of computer programming, the invention is described below with reference to operations that are performed by a computer system or a like electronic system. Such operations are sometimes referred to as being computer-executed. It will be appreciated that operations that are symbolically represented include the manipulation by a processor, such as a central processing unit, of electrical signals representing data bits and the maintenance of data bits at memory locations, such as in system memory, as well as other processing of signals. The memory locations where data bits are maintained are physical locations that have particular electrical, magnetic, optical, or organic properties corresponding to the data bits.

When implemented in software, the elements of the invention are essentially the code segments to perform the necessary tasks. The code segments can be stored in a processor readable medium, which may include any medium that can store or transfer information. Examples of the processor readable mediums include an electronic circuit, a semiconductor memory device, a read-only memory (ROM), a flash memory or other non-volatile memory, a floppy diskette, a CD-ROM, an optical disk, a hard disk, a fiber optic medium, a radio frequency (RF) link, etc. The term "module" may refer to a software-only implementation, a hardware-only implementation, or any combination thereof. Moreover, the term "third-party application servers" and "third-party applications" may both refer to the physical servers on which a third-party application may execute, or to the third-party application program itself.

EXAMPLARY EMBODIMENTS

Figure 1:
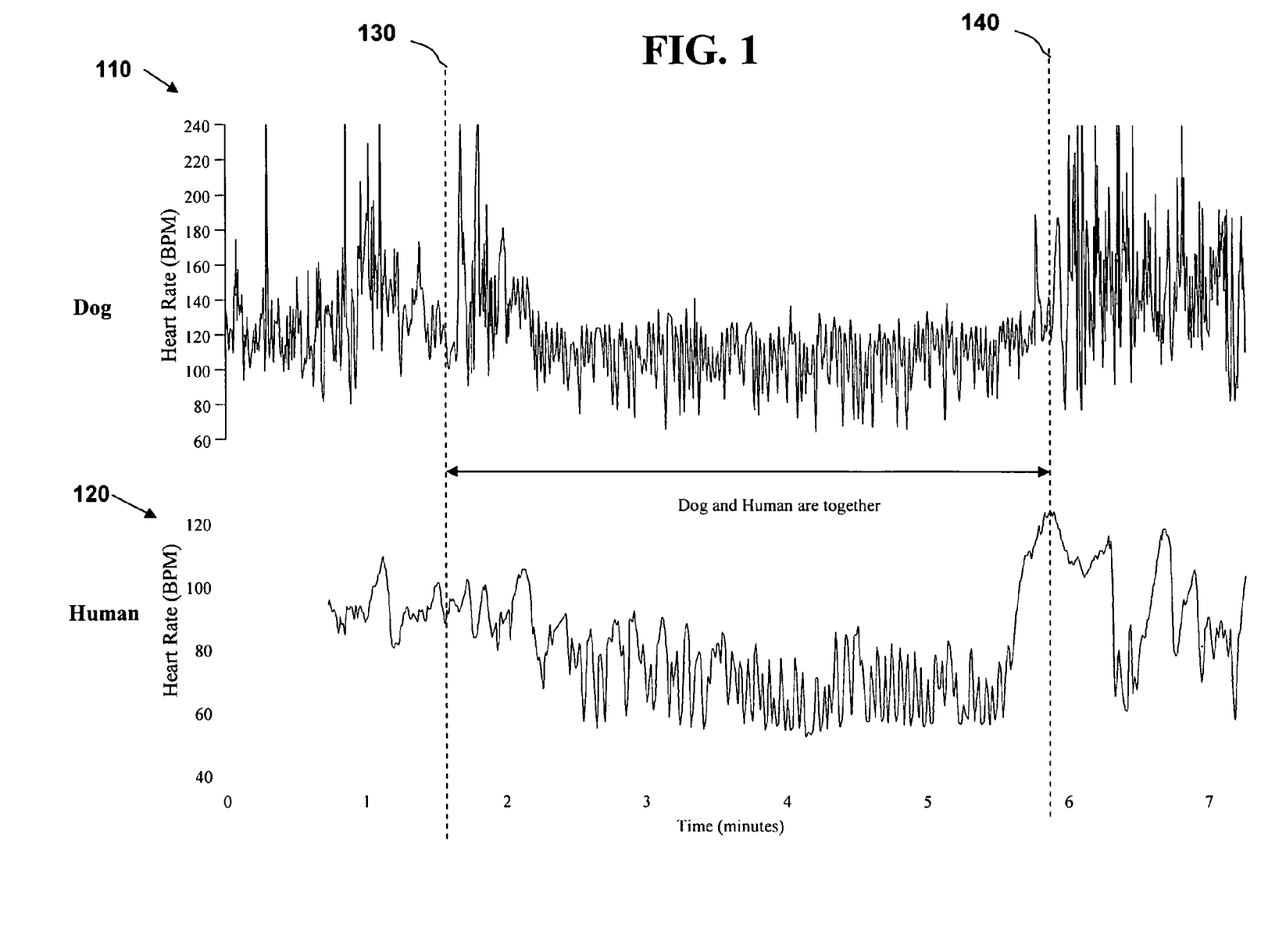
FIG. 1 illustrates a graph comparing the interaction between human and animal heart rates as a function of time.

To that end, FIG. 1 depicts a graph comparing the time domain signal of the heart rhythm pattern of a dog (plot 110) with the heart rhythm pattern of the dog's owner (plot 120) over a period of time. In this embodiment, both dog and human were fitted with ECG sensors. As shown, the experiment begins at t=0 with the dog and owner being in separate rooms. As shown, the HRV patterns 110 and 120 of both the dog and human appear to be relatively disorganized.

At time 130, the human enters the room and greets his dog. At this point there is a pronounced spike in the dog's HRV pattern 110, as shown in FIG. 1. The dog and his owner then enjoy each other's company from about the time 130 mark to close to the time 140 mark. During the period of time between time 130 and 140, it appears that HRV patterns 110 and 120 do indeed reflect a change in both the dog's and human's inner state. In particular, the HRV patterns 110 and 120 for both the dog and human shift to a much more coherent pattern. We deduce that animals, and possibly humans, are energetically sensitive to the fields produced by the heart. It should be noted that no physical contact took place during this period. There was, however, an intentional shift in emotional state by the human towards the dog, as evidenced by the more organized HRV pattern 120 of the human.

This is further supported by event shown at about the time 140 mark when the human gets up to leave the room. At this point, and for a period of time thereafter, both human and animal experience an increase in their HRV patterns, as well as much less organization. It further bears noting that disorganization of the dog's HRV pattern 110 after the time 140 mark is more pronounced than the level of disorganization prior to the time 130 mark. This is suggestive of the level of separation anxiety being experienced by the dog triggered by his owner leaving the room. Thus, changes in HRV pattern data may be correlated to a shift either toward or away from coherence.

It should further be appreciated that in certain embodiments, it may be desirable to provide feedback to the animal, the human or both. A variety of display formats may be employed, including detailed information, graphical information, graphic images, video images, and audio feedback. According to one embodiment, the level of coherence may control the volume on a music delivery system. Further, in one embodiment, the music changes style and/or pace with coherence level.

Similarly, coherence, as derived from HRV pattern analysis or respiration rhythms may be used to drive audio, video and/or specific gaming events. In particular, a decrease in coherence (which is associated with a negative mental/emotional state) would generate one type of feedback or gaming event, while an increase in coherence (associated with a positive mental/emotional state) would drive a difference type of feedback or gaming event.

Aside from coherency, all of the aforementioned disclosure is equally applicable to measuring and improving the overall emotional wellbeing of an animal, the animal's owner, or both. For example, emotional state may be measured using known physiological indicator(s) (e.g., animal skin conductance, heart rate, heart rate variability, HRV coherence and/or respiratory rate/pattern information), where resulting pattern data is compared or otherwise interpreted against known data. Such analysis may be carried out in the frequency domain, the time domain, using a non-linear approach, using period analysis, using template matching, etc.

Figure 2:
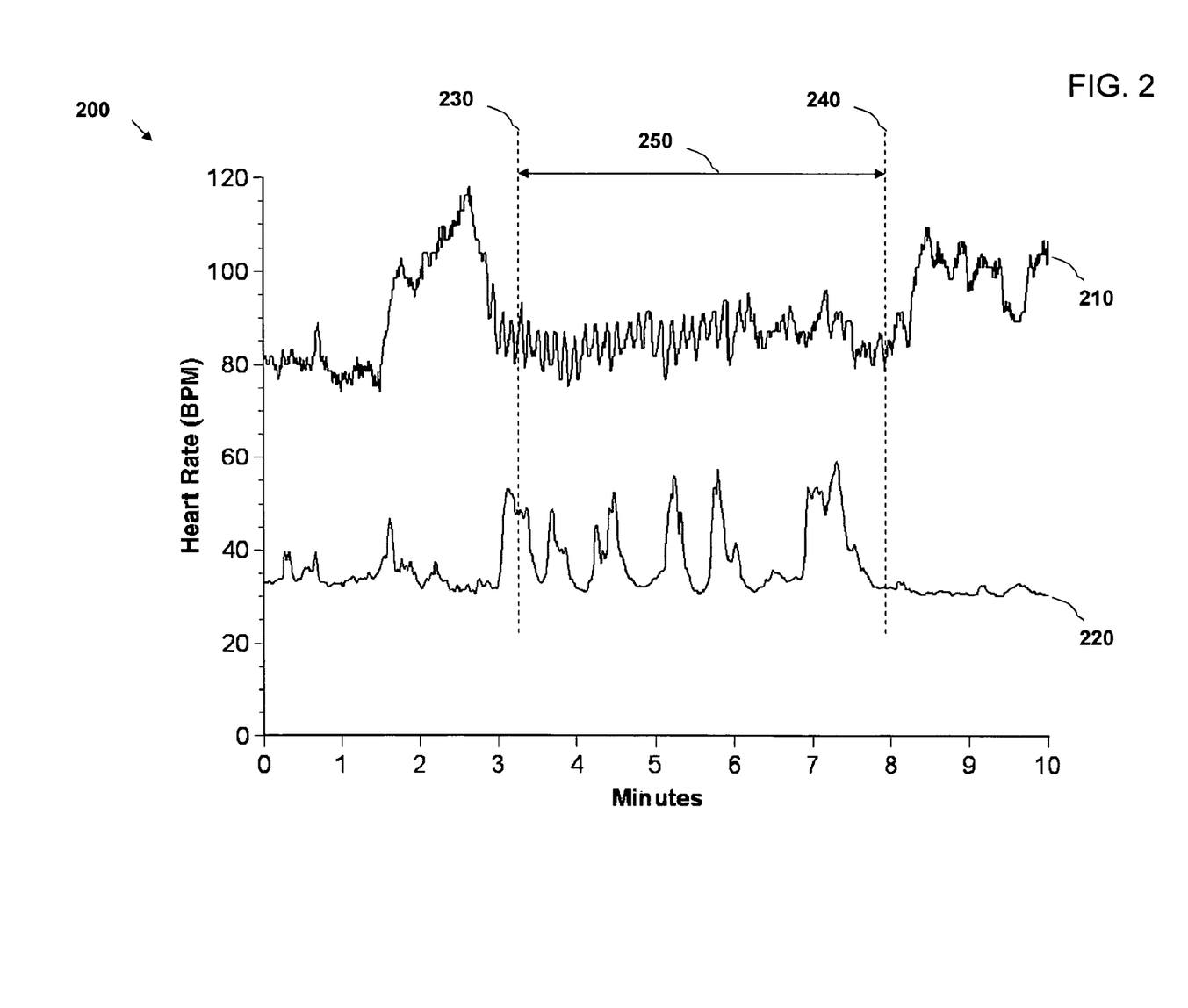
FIG. 2 illustrates another graph comparing the interaction between human and animal heart rates as a function of time.

Referring now to FIG. 2, depicted is a graph comparing the time domain signal of the heart rhythm pattern of a horse's owner (plot 210) with the heart rhythm pattern of the horse (plot 220) during a coherence synchronization session. In this embodiment, both the horse and human were fitted with ECG sensors.

As shown, at time 230 both the HRV patterns 210 and 220 begin to assume a more ordered pattern. This continues until approximately time 240, where again the patterns 210 and 220 assume a more disorganized structure. The period of time between time 230 and 240 is the coherence synchronization session 250. During this session 250, both the animal and human HRV patterns 210 and 220 undergo a pronounced pattern change from a relatively unstructured pattern, to one of higher order. To that, one embodiment is to detect a coherence synchronization between an animal and a human by recognizing and evaluating such HRV pattern changes.

Figure 3A:
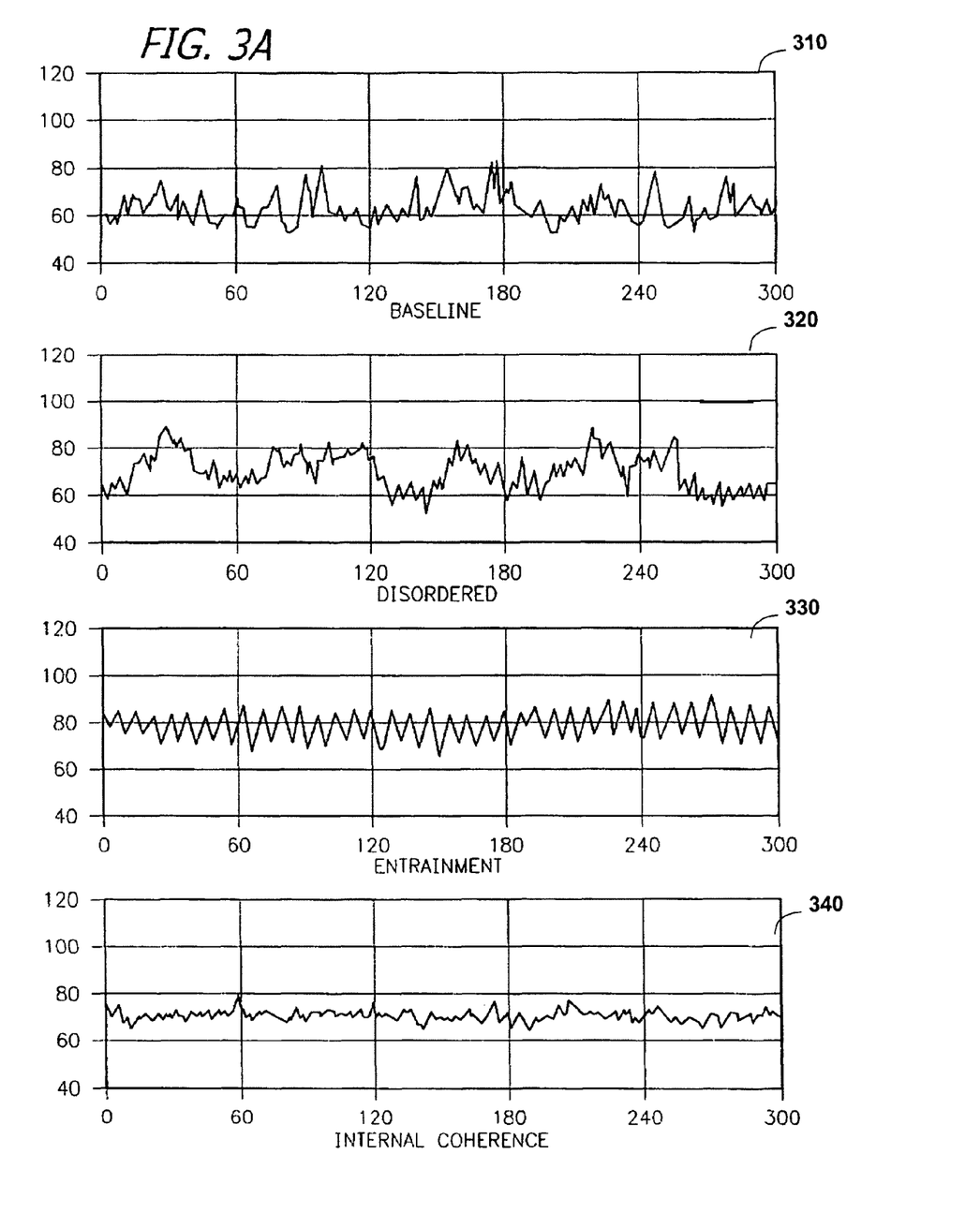
FIG. 3A illustrates the characteristic time domain HRV for four distinct physiological states.
Figure 3B:
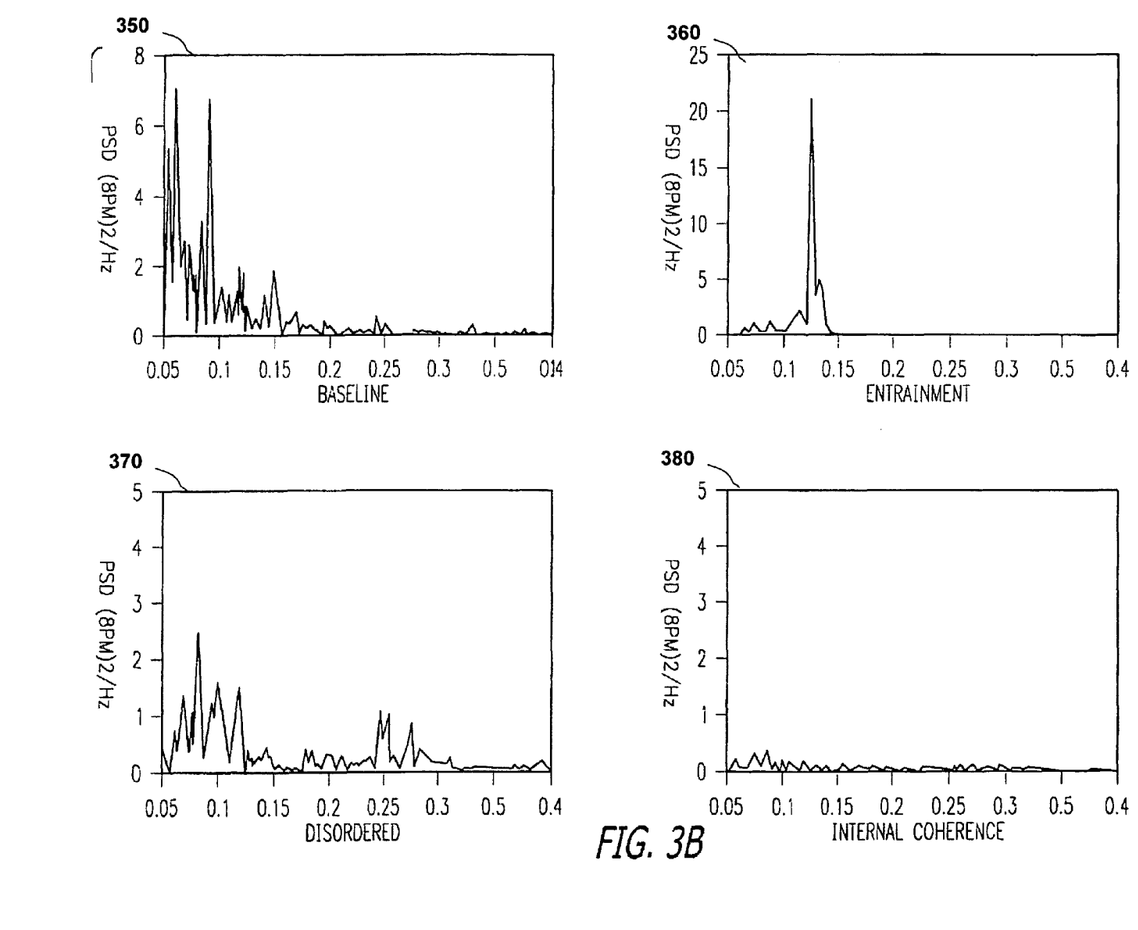
FIG. 3B illustrates the characteristic power spectrum distribution (PSD) corresponding to the time domain HRV for the four distinct physiological states of FIG. 3A

Referring now to FIG. 3A, shown is the time domain HRV of a subject in various emotional states, while FIG. 3B depicts the corresponding PSDs for each such emotional state. A baseline condition (graph 310 and 350) is considered to be when the subject is in a normal, resting state. A disordered state (graphs 320 and 370) is where the subject is feeling agitated emotions such as anger or fear. Note the more irregular nature of this waveform, clearly showing the lower frequency components contributed by the sympathetic system. In contrast, in a coherent state (graphs 330 and 360), the waveform is considerably more regular and orderly. Coherence is a condition which we have shown can be attained by following a conscious plan or protocol for effecting a positive emotional state, such as care, appreciation or love. According to one analysis methodology, coherence is achieved when synchronization occurs between the HRV waveform and other biological oscillators, such as respiration. Note that other correlations may be made between the HRV waveform, as well as other parameters of the heart rate and its variability, and the general state of the subject, including other physiological systems. Coherence, or internal coherence, (graphs 340 and 380) is a more ordered mental and emotional state in which more ordered and harmonious interactions among various physiological systems occurs. The principles of FIGS. 3A-3B has now been shown to apply to animal subjects, as well as humans.

Figure 4:
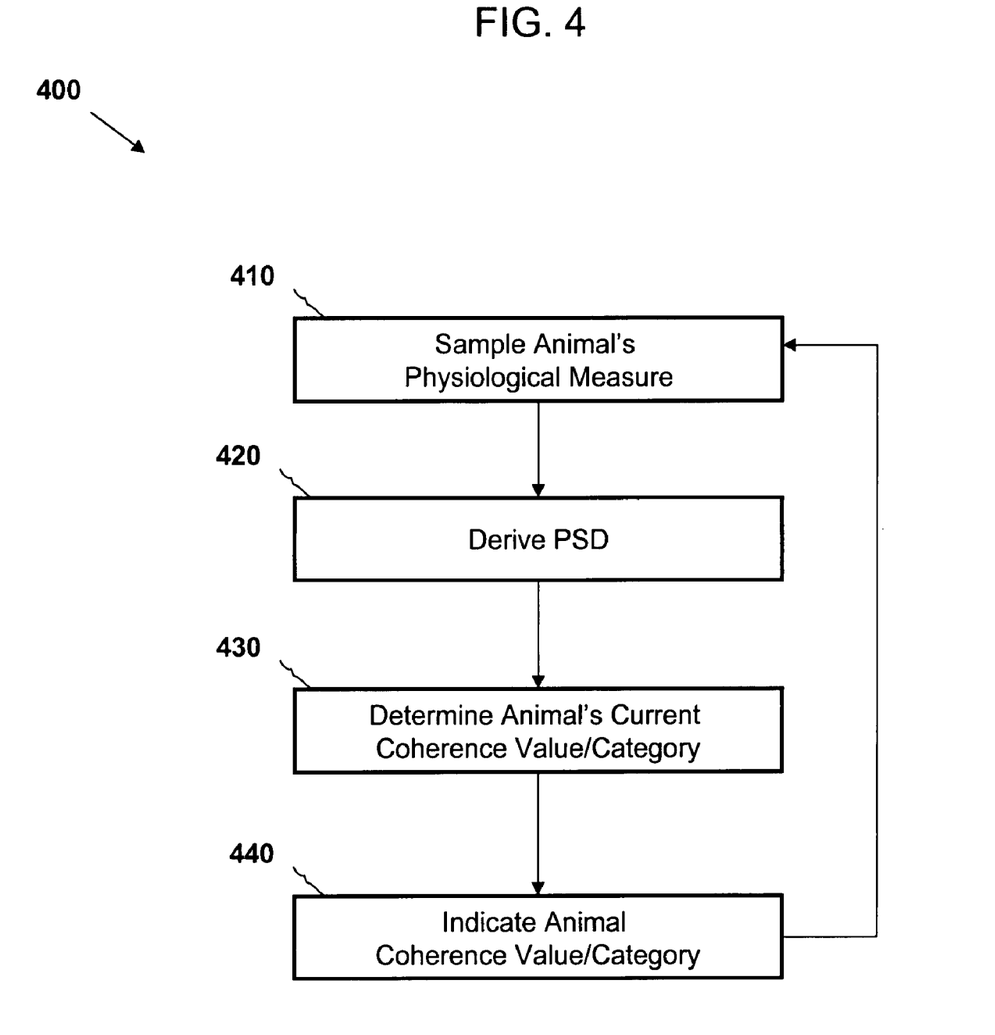
FIG. 4 is a process diagram for implementing one embodiment of the invention.

FIG. 4 illustrates a process for calculating a coherence value or category for an animal subject, and providing a corresponding coherence indication to a human subject. In general, the process involves monitoring the beat-to-beat changes in the animal subject's heart rate, calculating a coherence value, and presenting a representation of the categorization of the calculated value. The coherence value is determined by the power distribution of the HRV processed data, and the score is a historical indication of the coherence value.

Specifically, process 400 begins at block 410 where the a physiological measure of the animal subject is sampled, where said physiological measure may be any of respiratory sinus arrhythmia, heart rate variability, respiration patterns, blood pressure rhythms and a factor derived from ECG-R wave amplitudes. This sampling may involve using an electrical sensing apparatus, such as an electrocardiograph (ECG), light sensing apparatus, such as the photo plethysmographic sensor, or any other apparatus or means whereby each heart beat can be ascertained substantially in real time. For example, at regular time intervals, say 100 times per second, the output of a sensor is sampled and digitized using a conventional analog-to-digital (A/D) converter. The raw samples may then be stored. This raw data is basically a record of each heart beat and the relative time of its occurrence. The stored raw data can be thought of as comprising inter-beat-interval (IBI) information, from which the time interval between beats can be determined. It is the IBI variation which is generally referred to as "heart rate variability," or simply HRV.

At block 420 the PSD for the collected physiological data may be derived. In one embodiment, this may accomplished using the techniques described in detail in the parent application hereto. It should be appreciated that the PSD may be derived in either the frequency domain or the time domain.

Figure 6A:
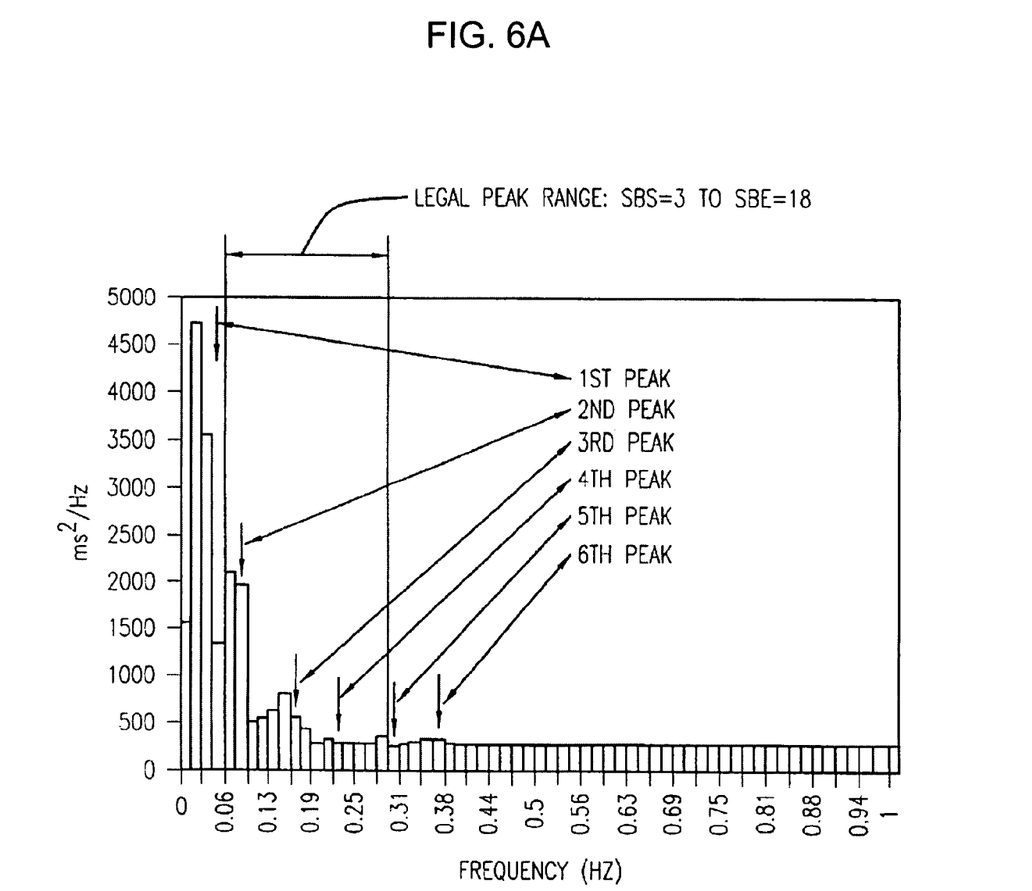
FIG. 6A-6C illustrate various PSD graphs corresponding to certain portions of the processes of FIGS. 4 and 5.

One embodiment of the result of block 420 is illustrated in FIG. 6A, where the horizontal axis represents frequency (Hz) and the vertical axis represents power (ms$^2$/Hz). Note that HRV data is portrayed in the form of a bar chart, wherein each bar represents the power contained in the HRV signal within a respective, narrow band of frequencies comprising a "bin," as illustrated. For convenience of reference, the bins are logically numbered sequentially, starting with bin 1 on the far left, and continuing to bin 64 on the far right, where each bin corresponds to a frequency. In one embodiment, user-selectable control variables may be used to select the range of bins from which the highest local peak will be selected. As it can be anticipated that the desired peak will be within a certain frequency range, it may not be necessary to consider the entire PSD. According to one embodiment, the starting search bin is selected by a variable "search bin start" (SBS), while the ending search bin is selected by a variable "search bin end" (SBE). For the example illustrated in FIG. 6A, the SBS is equal to 3 and the SBE is equal to 18, comprising the search range of bins 3, 4, 5, . . . ,18.

Once the PSD has been derived, process 400 may continue to block 430 where a coherence value or category may be determined. As previously mentioned, the coherence value is representative of the degree of ANS order in the animal subject, and a high coherence value is characterized by an increased synchronization the various oscillatory systems of the animal subject. In certain embodiments, the higher the coherence value or state, the more ordered the HRV waveform will be (e.g., sine-wave shape). One embodiment of how to determine the coherence value and/or category is described below with reference to the process of FIG. 5.

In another embodiment, the coherence category may be representative of a coherence change characterized as a shift in the HRV waveform's order. By way of example, FIGS. 1-2 show how the HRV pattern for an animal subject can shift from a chaotic state to an ordered state, and vice versa. To that end, rather than quantifying the coherence peak of the PSD as described above, in another embodiment, the coherence category determined at block 430 may instead correspond to a coherence shift or change in the HRV waveform pattern.

In any event, once the coherence value or category is determined at block 430, process 400 may then continue to block 440 where an indication of the animal subject's coherence (or shift in coherence) may be provided to a human, such as the animal's owner in the case of a pet subject. While in one embodiment, this coherence indication may be in the form of different sounds corresponding to the various coherence categories, different colored lights or LEDs, as well as LED illumination patterns, it should equally be appreciated that any other form of feedback may be similarly used. Moreover, the coherence indicator may be integrated with a collar or harness worn by the animal subject, or may be a remotely-located device which received the coherence information via a wireless connection with a sensor/transmitter device attached to the animal subject. Since the fields of physiological sensors, as well as wireless communications, are well developed and not particular to the invention, the details of such are not included herein.

It should be appreciated that process 400 may be iterative in that it provides a continuous indication of the current coherence value or state for the animal subject, as it may vary over time.

Figure 5:
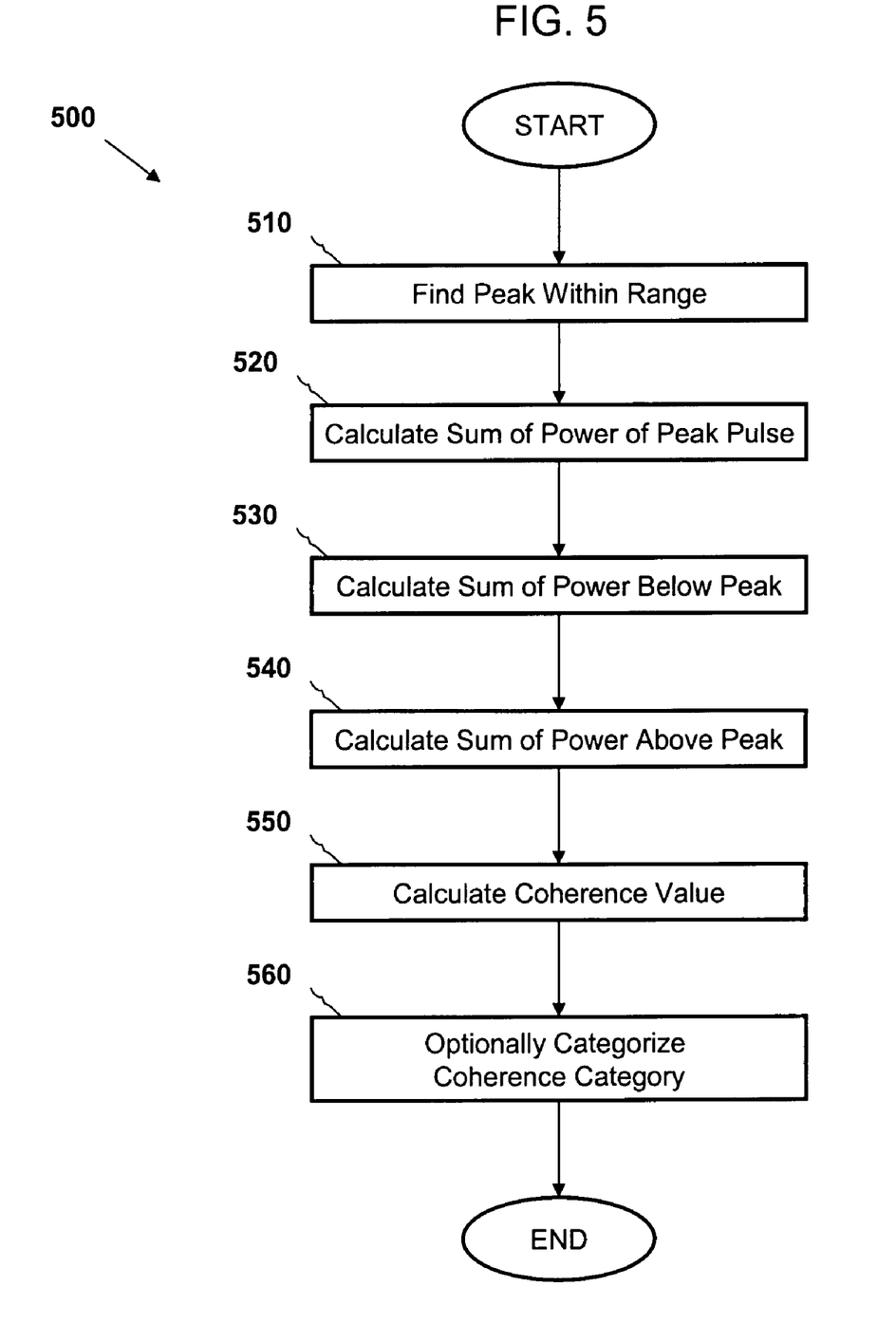
FIG. 5 is process diagram for implementing another embodiment of the invention.

Referring now to FIG. 5, depicted is one embodiment for determining the animal subject's current coherence state or category, as described above with reference to block 430 of FIG. 4. In particular, process 500 begins at block 510 where a search is made, within the selected bin range or window, for all local peaks in the HRV spectrum, each being represented by the single bin having the highest power level, i.e., the bin underneath the respective peak. Next, the bin representing the highest peak within the bin range is selected. In the example shown in FIG. 6A, there are three peaks within the bin range of bin 3 to bin 18. The highest peak is located at bin 5. Note that the first, and absolute largest, peak is represented by bin 2, so bin 3 is not considered to represent a peak.

Once the highest peak, or coherence peak, within the selected bin range has been determined at block 510, the sum of the power associated with the coherence peak may be calculated at block 520 which indicates the energy of the wave in the coherence peak in relation to the total energy in the PSD. To calculate the coherence peak power, the "width" of the peak is determined from a pair of user-selected variables—one of which defines the number of bins to the left of the peak bin ($P_{Below}$), the other of which may define the number of bins to the right of the peak bin ($P_{Above}$). Note that these variables may be different if an asymmetric distribution is desired. The total energy of the peak, $P_{Sum}$, may then be calculated as the sum of the power values of all bins in the range [(Peak−$P_{Below}$), (Peak+$P_{Above}$)].

Figure 6B:
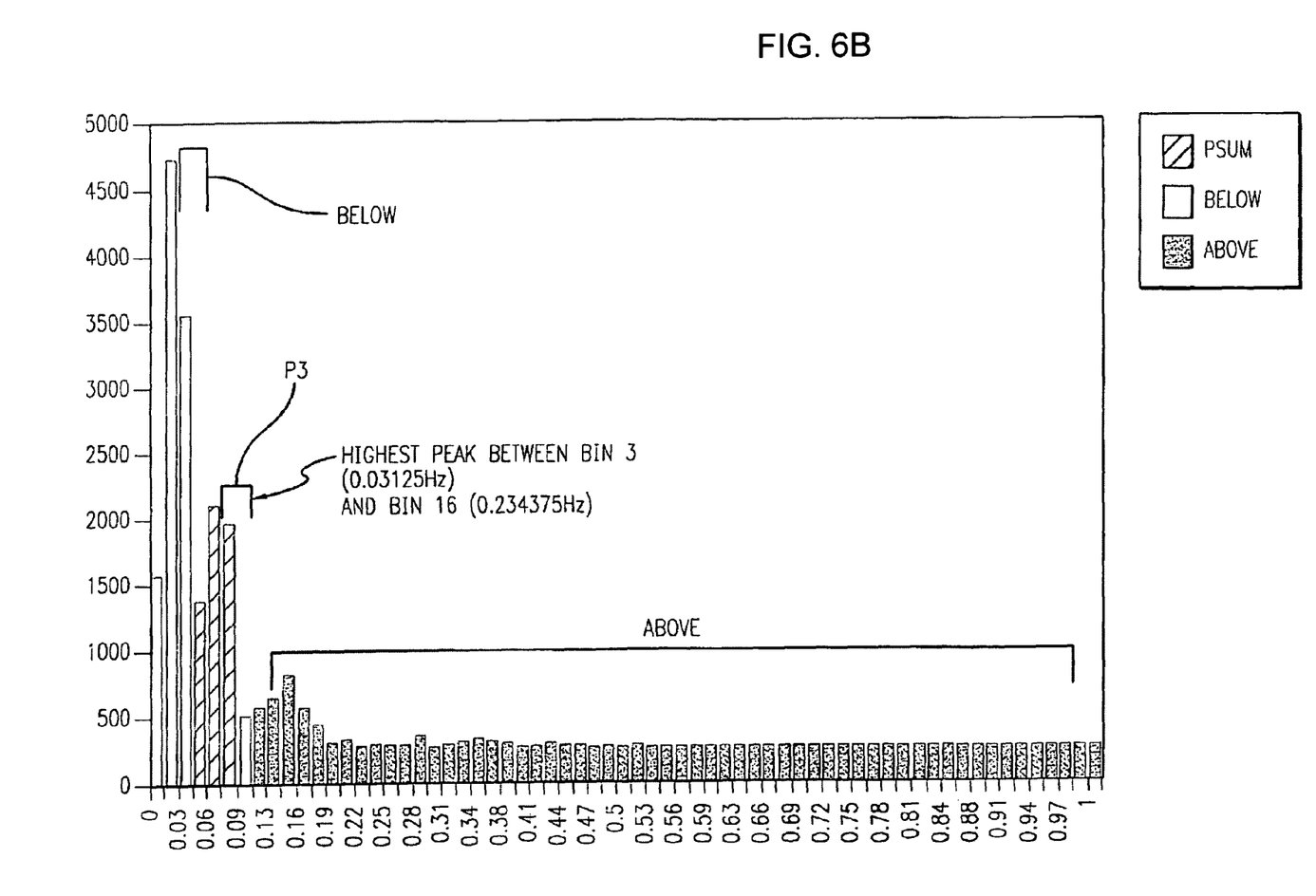

Process 500 continues to block 530 where the total power below the coherence peak ($P_{Below}$) is calculated. In one embodiment, the value of $P_{Below}$ is a summation of the power values of all bins in a range which may be user defined. Similarly, at block 540, the total power above the peak ($P_{Above}$) may be calculated within a relevant range, which again may be user-selected. The value of $P_{Above}$ is a summation of the power values of all bins in this, and is illustrated in FIG. 6B.

Figure 6C:
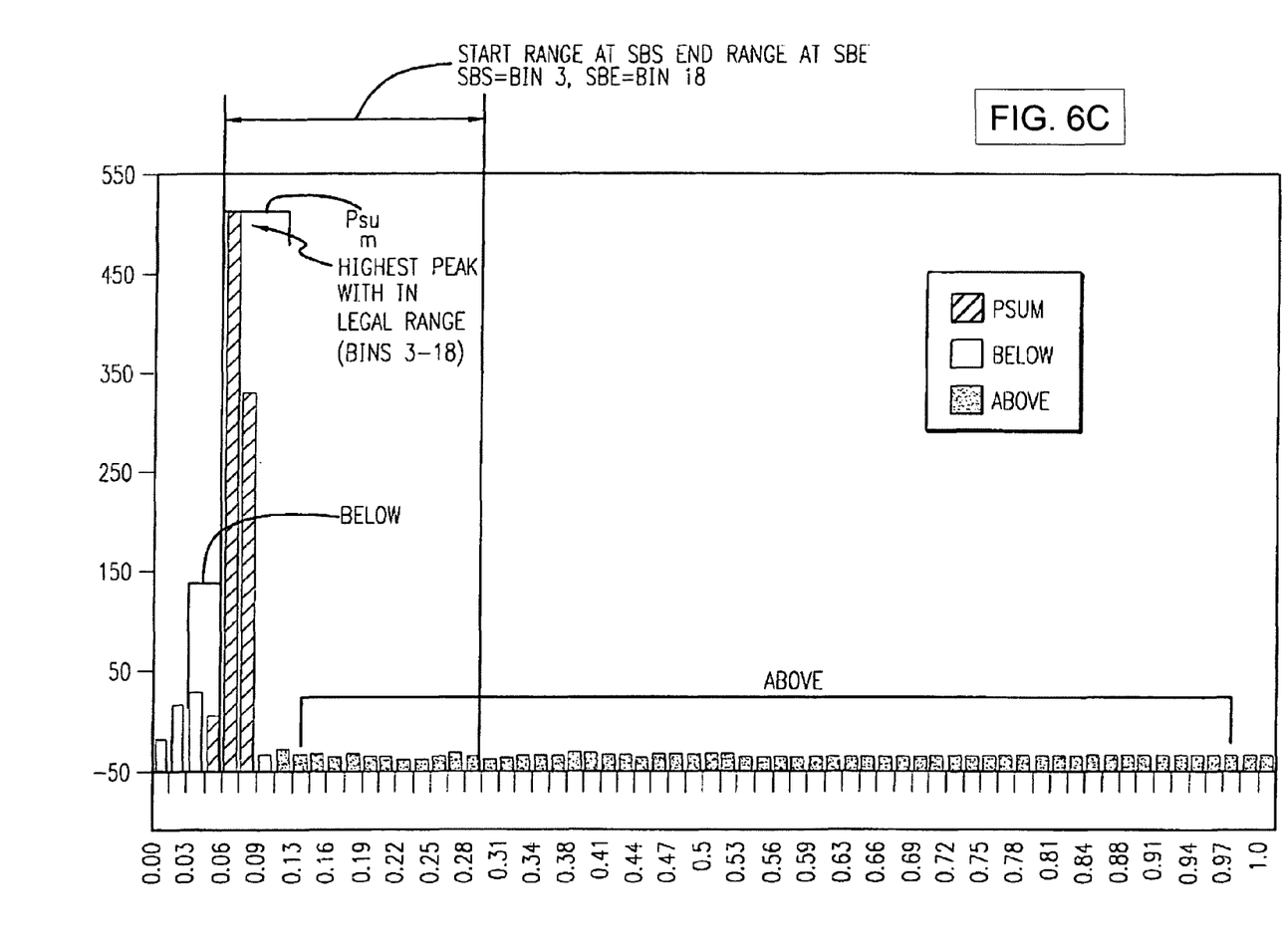

Thereafter, a coherence value may be calculated at block 550 according to the equation $(P_{Sum}/P_{Below})*(P_{Sum}/P_{Above})$. However, it should equally be appreciated that the coherence value of block 550 may be calculated according to any approach which produces a value representative of the relative power in the coherence peak to the overall power in the PSD. In one embodiment, maximum coherence is reached when the coherence peak contains a very large portion of the total power. A particularly high coherence value is illustrated in FIG. 6C, where $P_{Sum}$ is high as compared to both $P_{Below}$ and $P_{Above}$.

While in one embodiment, the coherence value calculated at block 550 may be used in the operation of block 440 of FIG. 4 described above, in another embodiment it may be used to select a coherence category. To that end, process 500 may proceed to optionally categorize the coherence value of block 550 into a coherence category at block 560. In one embodiment, this may be accomplished using user-selected coherence threshold values. For example, three categories of coherence may be defined using two variables, Threshold 1 and Threshold 2, each of which represents a respective coherence value. In such an embodiment, a coherence value from block 550 below Threshold 1 may indicate the animal subject is considered as not having achieved significant entrainment, and would be in the low coherence category. For a coherence value above Threshold 1 but below Threshold 2, the animal subject may be considered to have mild coherence. For a coherence value above Threshold 2, the animal subject may be considered to have achieved high coherence. It should of course be appreciated that more or fewer categories of coherence may be used in accordance with the principles of the invention.

Where a coherence category has been determined, the indication provided above at block 440 of FIG. 4 may be a category indication rather than a coherence value indication. Additionally, as previously mentioned, the indication may be in the form of different sounds corresponding to the various coherence categories, different colored lights or LEDs, LED illumination patterns, etc.

Figure 7:
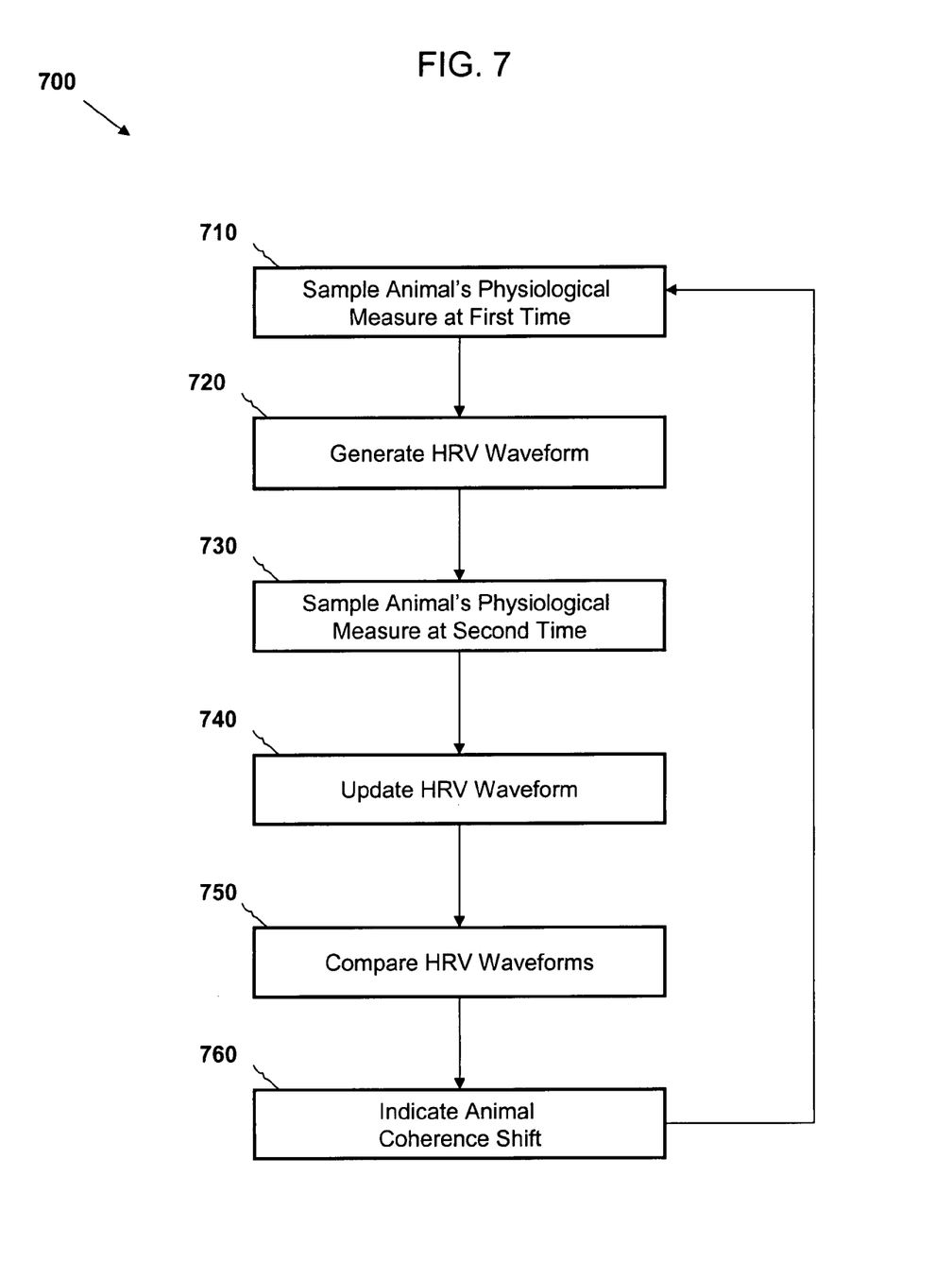
FIG. 7 is process diagram for implementing still another embodiment of the invention.

FIG. 7 illustrates a process for indicating a coherence shift for an animal subject. The process 700 begins at block 710 where the a physiological measure of the animal subject is sampled at a first point in time. As described above, the physiological measure may be any of respiratory sinus arrhythmia, heart rate variability, respiration patterns, blood pressure rhythms and a factor derived from ECG-R wave amplitudes. This sampling may involve using an electrical sensing apparatus, such as an electrocardiograph (ECG), light sensing apparatus, such as the photo plethysmographic sensor, or any other apparatus or means whereby each heart beat can be ascertained substantially in real time. It should be appreciated that the sampling operation of block 710 may occur over some sampling period. The data derived from the sampling may correspond to inter-beat-interval (IBI) information, from which the time interval between beats can be determined and used to represent HRV.

At block 720, an HRV waveform may be generated from the sampling of block 710 above. It should be appreciated that the HRV waveform may be generated in either the frequency domain or the time domain.

Thereafter, another period of sampling may be performed at a second point in time at block 730. Again, this sampling may occur over some sampling period. As shown in FIG. 7, the data derived from the sampling of block 730, may be used to update the HRV waveform generated above at block 720 with the IBI information corresponding to this second sampling operation.

Process 700 may then continue to block 750 where the HRV waveform generated at block 720 may be compared to the updated waveform of block 740. In one embodiment, this comparison may be performed to detect a shift in the amount of order in the HRV waveform from, for example, an ordered state or a less ordered or vice versa. This comparison may provide information on whether the animal subject is moving towards or away from a state of coherence.

Based on the comparison of block 750, process 700 may continue to block 760 where an indication of the animal subject's coherence shift, if any, may be provided to a human, such as the animal's owner in the case of a pet subject. While in one embodiment, this coherence indication may be in the form of different sounds corresponding to the various coherence categories, different colored lights or LEDs, as well as LED illumination patterns, it should equally be appreciated that any other form of feedback may be similarly used. As with the aforementioned embodiments, the coherence indicator may be integrated with a collar or harness worn by the animal subject, or may be a remotely-located device which received the coherence information via a wireless connection with a sensor/transmitter device attached to the animal subject.

It should be appreciated that process 700 may be iterative in that it provides a continuous indication of any coherence shifts for the animal subject, as they may occur over time.

As previously mentioned, another aspect of the present disclosure is the simultaneous measurement of human (e.g.; pet owner) and animal physiological indicators to detect and/or measure the level of synchronization, coherence or other indicators of physiological or emotional linkage between the animal and the human. To that end, both human and animal HRV may be simultaneously measured in accordance with the teachings herein, with the resulting coherence data being analyzed for possible synchronized coherence. The amount of synchronization between the human coherence value and the animal coherence value may then be output in the same manner described above with respect to the coherence categories. That is, the synchronization between the human and animal coherence may be assigned difference categories, such as high level, medium and low. This information may then be provided as feedback in the form of predefined sounds, LED colors and/or LED illumination patterns.

It should be noted that many methods can be used to characterize state change within a signal, and thus be used to track coincident state changes between two signals, such as the HRV of a human and the HRV of an animal or pet.

As previously mentioned, another aspect of the invention is the notion of detecting and indicating meta-coherence when present. That is, if one signal changes in some way generally coincident with changes in the second signal, but the two signals in question are quite different from each other in the time and thus frequency domains, then "coincident changing" could be defined as a kind of meta-coherence, rather than the close tracking of one signal by the other in the time or frequency domain. Thus, meta-coherence could exist between two signals even if neither was individually representative of a state of coherence.

Following are some example ways of characterizing state change in a particular signal (e.g., animal HRV waveform), and which therefore provide a means of characterizing meta-coherence between two signals consistent with the principles of the invention.

Where the two signals in question, such as animal and human HRV signals, are fairly similar, one may compute a running cross correlation between the two signals of interest in the time domain, or a running correlation for multiple bands in the frequency domain. Alternatively, a related method may involve template matching (or computing the Euclidean distance or some other metric of distance) between successive spectrums. This may be an example of what is known as a non-parametric method.

On the other hand, there may be cases in which the two HRV signals (such as one derived from an animal, and the other from a human) are quite dissimilar in both the time and consequently the frequency domains, and thus where running correlations or spectral template matching may not yield useful information.

To that end, another approach may be to model each signal by what is known as an autoregressive (AR) process or filter. This involves generating (or finding) filter coefficients which best predict the current value of a signal based upon a weighted sum of some optimal number of its past values. Linear predictive filters work according to this principle. They are most often implemented in the time domain, although they have frequency domain equivalents. The changing Euclidian (or some other metric of) distance between successive sets of coefficients over time could be used to indicate state change in each signal. This AR process may be known as a parametric method.

A more sophisticated variant of the parametric AR process which can be used to detect state changes in time series (such as the EEG or HRV) is known as the Generalized Autoregressive Conditional Heteroscedasticity (GARCH) model. Both the AR and GARCH methods are especially appropriate for real-time monitoring.

So-called Kalman filters may similarly be used to provide a cross-correlation between two dissimilar signals. The Kalman filter coefficients generated during the sampling process (e.g., on a sample-by-sample basis) may be used to generate constantly updated HRV spectrums. The resulting spectrums can then be decomposed in LF, MF and HF components, and thus various HRV derived parameters, such as the sympathetic and parasympathetic activity, LF/HF ratio (sympathovagal balance) and RSA can be tracked and correlated in real-time as well. A variant of the Kalman filter is the Recursive Least Squares or RLS filter.

Therefore, physiological variables including but not limited to sympathetic and/or parasympathetic activity could be tracked between animals and humans. Assuming that the HRV spectral bands corresponding to sympathetic and/or parasympathetic activity are different in different biological organisms, then the tracking between human and animal could take place on the basis of coincident shifts in the direction of sympathetic and/or parasympathetic activity rather than requiring particular HRV frequency bands in one signal to track particular frequency bands in the other. However, as suggested below, the basis of comparison or tracking can even be defined in a more abstract manner, by simply tracking coincident (or even delayed) change, rather than changes in particular HRV spectral bands relating to defined physiological parameters.

It should further be appreciated that the method of nonlinear dynamical factor analysis for state change detection may be used. While this type of method may not be able to detect state change as quickly as some the above-described AR based techniques, it may be useful in identifying non-linear components within each HRV series, as well as changing non-linear relationships between the two signals.

Other non-linear methods with potential applicability to tracking coherence state changes include but are not limited to: Correlation Dimention (CD), Largest Lyapunov Exponent (LLE), Hurst Exponent (H) and Approximate Entropy (ApEn).

In certain embodiments, if both HRV signals have changed beyond a preset threshold in any specified unit of time, then a "coincident" change could be said to have occurred between both signals. If some pre-defined number of coincident changes have been exceeded for some unit of time, then a state of "meta-coherence" could be said to have been attained. The strength of this approach lies in the robustness of the coefficient estimation process coupled with the rapidity with which the coefficients can be updated to reflect changes in HRV state, even when the two HRV signals do not resemble each other in the time and frequency domain.

It should further be appreciated that the principles described herein may similarly be applied to more than two signals such as multiple HRV time series, and thus be effectively employed to define a concept of group heart coherence (GHC) or group heart dynamics (GHD), or what may be referred to as accordance.

While portions of this disclosure have been in terms of the frequency domain, it should equally be appreciated by one skilled in the art that equivalent operations may be performed in the time domain and all references herein to frequency are intended to cover their time domain equivalent(s). In particular, the various HRV signals referred to herein may also be characterized in terms of a repeating series of heart rate accelerations and decelerations in the time domain.

In one embodiment, one may "detrend" the signal by measuring the distance in time between each successive pair of zero crossings of the HRV wave pattern and divide by two. The average of all of the resulting values may then be calculated. The reciprocal of this average may be used as a rough estimation of the fundamental frequency of the time series. If the frequency is within some arbitrarily pre-defined range, then an event (e.g., coherency) may be said to have occurred.

In another exemplary embodiment, one may measure the distance in time between successive peaks (or valleys) between which the signal crossed zero (again the HRV waveform). Again, the average of all of the resulting values may be determined, and the reciprocal of this average used to provide a rough estimation of the fundamental frequency of the time series. Again, where the frequency is within some pre-defined range, a particular event (e.g., coherency) may be said to have occurred.

Additionally, a cross correlation may be performed between the HRV time series and one or more time domain templates. This can be performed as a series of contiguous blocks or on a running average basis. In the event the cross correlation is above some user-defined (optionally adjustable for challenge levels) threshold, then a state or event such as coherency can be defined to have occurred.

It should further be appreciated that each of the above techniques can be "scored" or otherwise evaluated in a number of ways. For example, one way would be to count the number of times (within some predetermined period of time) that the event or state in question has occurred. This could be on the basis of contiguous blocks of time, or computed as a running average. If the number of times that the state or event occurred is determined to be above some pre-defined threshold, then a "scored event" could be defined to have occurred. In one embodiment a scored event may be assigned a higher degree of confidence that the state or event has actually occurred.

It should further be appreciated that, in each of the above examples, the event or state determined to have occurred may be further classified into, for example, high, medium, low, or the like.

In still another embodiment, autocorrelation may be performed in which a measure is determined for how well a signal matches a time-shifted version of itself, as a function of the amount of time shift. More precisely, it is the cross-correlation of a signal with itself. Autocorrelation may be a useful technique for finding repeating patterns in a signal, such as determining the presence of a periodic signal which has been buried under noise, or identifying the missing fundamental frequency in a signal implied by its harmonic frequencies.

In still another embodiment, a linear predictive filter using a Least Mean Squared (LMS) algorithm may be used as yet another time domain analysis method. In this embodiment, this filter can be implemented in the time domain and can be used to characterize changes within a time series, or repeating series of heart accelerations and decelerations. The coefficients thus generated by the linear predictive filter can be analyzed in the frequency domain yielding the frequency spectrum of the time series. In one embodiment, the linear predictive filter may be related to the autoregressive (AR) approach mentioned above for characterizing meta-coherence.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A method for detecting physiological coherence in an animal subject comprising the acts of:
    sampling a physiological measure of the animal subject;
    deriving a power spectrum distribution (PSD) from the physiological measure;
    tracking dynamically a PSD peak within a predetermined range where the PSD peak has a relative amplitude to a plurality of other peaks in the PSD;
    determining a current coherence value based on said relative amplitude and corresponding to the animal subject's automatic nervous system (ANS) activity;
    determining, by a processor, a current coherence category for the animal subject from a plurality of coherence categories which correspond to the current coherence value; and
    providing a coherence category indication associated with the current coherence category.

2. The method of claim 1, wherein the current coherence value increases as ANS order increases, and is further characterized by an increased synchronization between two or more oscillatory systems of said animal subject.

3. The method of claim 1, wherein sampling the physiological measure comprises sampling the physiological measure where said physiological measure comprises at least one of respiratory sinus arrhythmia, heart rate variability, respiration patterns, blood pressure rhythms and a factor derived from ECG-R wave amplitudes.

4. The method of claim 1, wherein the plurality of coherence categories correspond to a shift in a pattern of the PSD.

5. The method of claim 1, wherein sampling further comprises analyzing the physiological measure in one of a frequency domain and a time domain.

6. The method of claim 1, wherein said relative amplitude is an amplitude ratio of a PSD peak amplitude to a plurality of amplitudes for said plurality of other peaks in the PSD.

7. The method of claim 1, wherein providing the coherence category indication comprises illuminating a light emitting diode having at least one of a color and an illumination pattern corresponding to the current coherence category.

8. The method of claim 1, further comprising:
    determining a coherence category for a human subject associated with the animal subject; and
    providing an indication of the coherence synchronization between the human subject and the animal subject.

9. A system for detecting physiological coherence in an animal subject comprising:
    a sensor adapted to sample a physiological measure of an animal subject;
    a coherence indicator configured to provide at least one of a visual and audible indication; and
    a processor coupled to the sensor and to the coherence indicator, the processor configured to:
        derive a power spectrum distribution (PSD) from the physiological measure,
        track dynamically a PSD peak within a predetermined range where the PSD peak has a relative amplitude to a plurality of other peaks in the PSD,
        determine a current coherence value based on said relative amplitude and corresponding to the animal subject's autonomic nervous system activity (ANS),
        determine a current coherence category for the animal subject from a plurality of coherence categories which corresponds to the current coherence value, and
        provide a coherence category indication to the coherence indicator that is associated with the current coherence category.

10. The system of claim 9, wherein the current coherence value increases as ANS order increases, and is further characterized by an increased synchronization between two or more oscillatory systems of said animal subject.

11. The system of claim 9, wherein the physiological measure comprises at least one of respiratory sinus arrhythmia, heart rate variability, respiration patterns, blood pressure rhythms and a factor derived from ECG-R wave amplitudes.

12. The system of claim 9, wherein the plurality of coherence categories correspond to a shift in a pattern of the PSD.

13. The system of claim 9, wherein the physiological measure is analyzed in one of a frequency domain and a time domain.

14. The system of claim 9, wherein said relative amplitude is an amplitude ratio of a PSD peak amplitude to a plurality of amplitudes for said plurality of other peaks in the PSD.

15. The system of claim 9, wherein the coherence category indication includes a light emitting diode having at least one of a color and an illumination pattern corresponding to the current coherence category.

16. The system of claim 9, wherein the processor is further configured to,
    determine a coherence category for a human subject associated with the animal subject, and
    provide an indication of the coherence synchronization between the human subject and the animal subject.

17. A method for detecting a physiological coherence shift in an animal subject comprising the acts of:
    sampling, at a first time, a physiological measure of the animal subject;
    generating a heart rate variability (HRV) waveform based on said sampling at the first time, wherein the HRV waveform has a first pattern;
    sampling, at a second time, the physiological measure of the animal subject;
    updating the HV waveform based on said sampling at the second time, wherein the HRV waveform has a second pattern;
    comparing, by a processor, the first pattern to the second pattern to detect a coherence change in the animal subject;
    providing a coherence indication associated with said coherence change.

18. The method of claim 17, wherein comparing comprises comparing an amount of order in the first pattern to an amount of order in the second pattern.

19. The method of claim 18, wherein providing the coherence indication comprises indicating a shift towards coherence when the amount of order in the second pattern is higher than the amount of order in the first pattern.

20. The method of claim 17, wherein sampling at the first time and at the second time further comprises analyzing the physiological measure in one of a frequency domain and a time domain.

21. The method of claim 17, wherein providing the coherence indication comprises illuminating a light emitting diode having at least one of a color and an illumination pattern corresponding to the current coherence category.

22. The method of claim 17, further comprising:
determining a corresponding coherence change in a human subject associated with the coherence change in the animal subject; and
providing an indication of the coherence synchronization between the human subject and the animal subject.

* * * * *